(12) United States Patent
Faulkner et al.

(10) Patent No.: US 6,892,088 B2
(45) Date of Patent: May 10, 2005

(54) COMPUTER-ASSISTED BONE DENSITOMETER

(75) Inventors: Kenneth G. Faulkner, Verona, WI (US); Howard S. Barden, Madison, WI (US)

(73) Assignee: General Electric Company, Schenectady, NY (US)

( * ) Notice: Subject to any disclaimer, the term of this patent is extended or adjusted under 35 U.S.C. 154(b) by 150 days.

(21) Appl. No.: 10/065,109

(22) Filed: Sep. 18, 2002

(65) Prior Publication Data

US 2004/0068166 A1 Apr. 8, 2004

(51) Int. Cl.[7] ............................. A61B 5/05; G01N 23/06
(52) U.S. Cl. ............................................. 600/407; 378/51
(58) Field of Search ............................. 600/407, 160, 600/425, 430, 385, 436; 378/4, 5, 50, 84, 88, 87, 86, 51, 54; 424/4

(56) References Cited

U.S. PATENT DOCUMENTS

| | | | | |
|---|---|---|---|---|
| 4,858,128 A | * | 8/1989 | Nowak | 382/131 |
| 4,922,915 A | * | 5/1990 | Arnold et al. | 382/128 |
| 5,003,980 A | * | 4/1991 | Loo et al. | 600/407 |
| 5,138,553 A | | 8/1992 | Lanza et al. | |
| 5,306,306 A | * | 4/1994 | Bisek et al. | 600/407 |
| 5,348,009 A | * | 9/1994 | Ohtomo et al. | 600/407 |
| 5,480,439 A | | 1/1996 | Bisek et al. | |
| 6,002,959 A | | 12/1999 | Steiger et al. | |
| 6,038,281 A | | 3/2000 | Mazess | |
| 6,160,866 A | * | 12/2000 | Mazess et al. | 378/56 |
| 6,246,745 B1 | | 6/2001 | Bi et al. | |
| 6,418,183 B1 | | 7/2002 | Fox et al. | |
| 6,436,201 B1 | * | 8/2002 | Sugita et al. | 148/241 |
| 6,438,201 B1 | | 8/2002 | Mazess et al. | |

* cited by examiner

*Primary Examiner*—Daniel Robinson
(74) *Attorney, Agent, or Firm*—Quarles & Brady LLP; Carl Horton

(57) ABSTRACT

An x-ray densitometry system provides computer assistance to the operator in identifying possible sources of scanning or analysis error through computer review of the acquired data, operator input, and the ultimate diagnostic outputs.

22 Claims, 3 Drawing Sheets

COMPUTER-ASSISTED BONE DENSITOMETER

BACKGROUND OF INVENTION

The present invention relates generally to x-ray bone densitometers for measuring bone health and particularly to a bone densitometer providing computer assisted detection of measurement artifacts and operator errors.

X-ray bone densitometers make measurements at two x-ray energies to provide separate attenuation images of two basis materials, typically bone and soft tissue. The bone attenuation image is substantially free from attenuation caused by soft tissue allowing areal bone density (g/cm$^2$) to be accurately determined in vivo for assessments of bone strength and health. The bone attenuation image also provides improved definition of bone outlines, allowing measurements, for example, of bone morphology (e.g., vertebral height) such as may be useful for detecting crush fractures associated with osteoporosis.

In order to achieve accurate quantitative results from a bone densitometer, the patient must be properly positioned, motionless during the scan, and free from high-density materials such as pins or buttons. For proper analyses of the scanned data, the measurement regions may need to be correctly identified by the operator.

if a problem with the scan is not detected promptly, the patient may need to be recalled and scanned again, incurring additional expense and inconvenience. It is also possible that improper scanning may not be recognized at all, producing an erroneous result.

SUMMARY OF INVENTION

The present invention provides computer-assisted densitometry in which software monitors the steps of acquiring and analyzing the data with the intent of identifying potential positioning and/or analysis errors. This computer assistance provides a backup to the operator or physician review of the measurement, advising them of a possible problem. Computer assistance together with the oversight of the physician or operator may significantly decrease errors in the acquisition and analysis of the data, and decrease errors from any other source that affects the ultimate clinical measurement.

DETAILED DESCRIPTION

Figure 1:
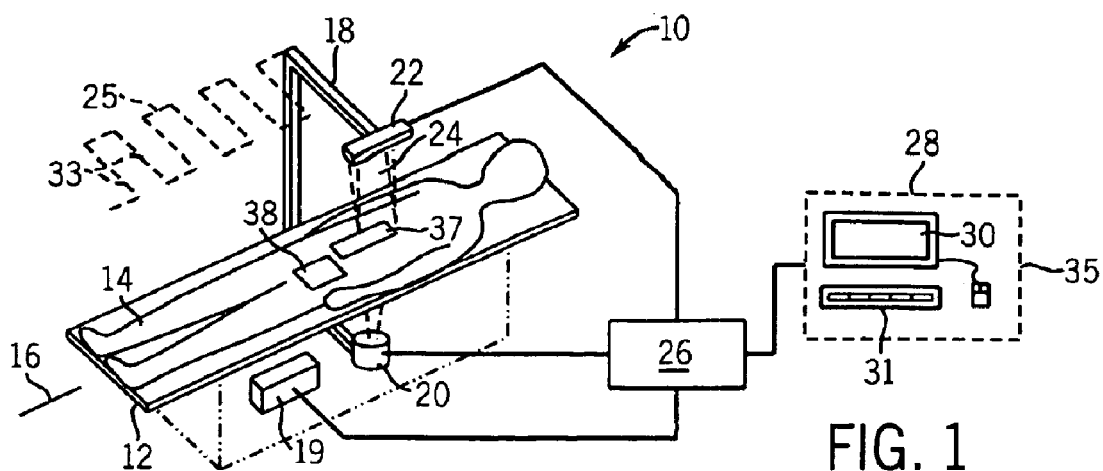
FIG. 1 is a simplified perspective view of a bone densitometer performing a posteroanterior or lateral scan of a patient with a fan beam under the control of a computer.

Referring now to FIG. 1, a bone densitometer, 10, includes a patient table, 12, providing a horizontal surface for supporting a patient in supine or lateral position along a longitudinal axis 16.

A C-arm 18, has a lower end positioned beneath the patient table 12 to support an x-ray source 20 and an upper end positioned above the patient table 12 supporting an x-ray detector 22. The x-ray source 20 and x-ray detector 22 may be moved in a raster pattern 25 so as to trace a series of transverse scans 33 of the patient during which dual energy x-ray data are collected by the x-ray detector 22. This raster motion is produced by actuators under control of a translation controller 19 according to methods well understood in the art.

In the preferred embodiment, the x-ray source 20 provides two x-ray energies and the x-ray detector 22 is a multi-element CZT detector providing for energy discrimination. However, other methods of dual energy measurement including those providing for rotating filter wheels or variations in x-ray tube voltage may also be used.

The x-ray source 20 produces a fan beam 24 whose plane is parallel to the longitudinal axis 16. The raster pattern 25 is adjusted so that there is a slight overlap between successive scan lines of the fan beam 24 as will be described below.

The x-ray source 20, x-ray detector 22, and translation controller 19 communicate with and are under the control of computer 26 which may include both dedicated circuitry and one or more processors having the ability to execute a stored program portions of which will be described in detail below.

The computer 26 communicates with a terminal 28 including a display 30 and a keyboard 31 and a cursor control device such as a mouse 35 allowing for operator input and the output of text and images to the operator as is well understood in the art.

In operating the bone densitometer 10, the computer 26 will communicate with the translation controller 19 to scan a region of the patient in one or more transverse scans 33 during which a number of scan lines 34 of data will be collected, each with a different ray of the fan beam 24. These data will include attenuation measurements at two distinct energy levels.

Figures 2, 3, 4:
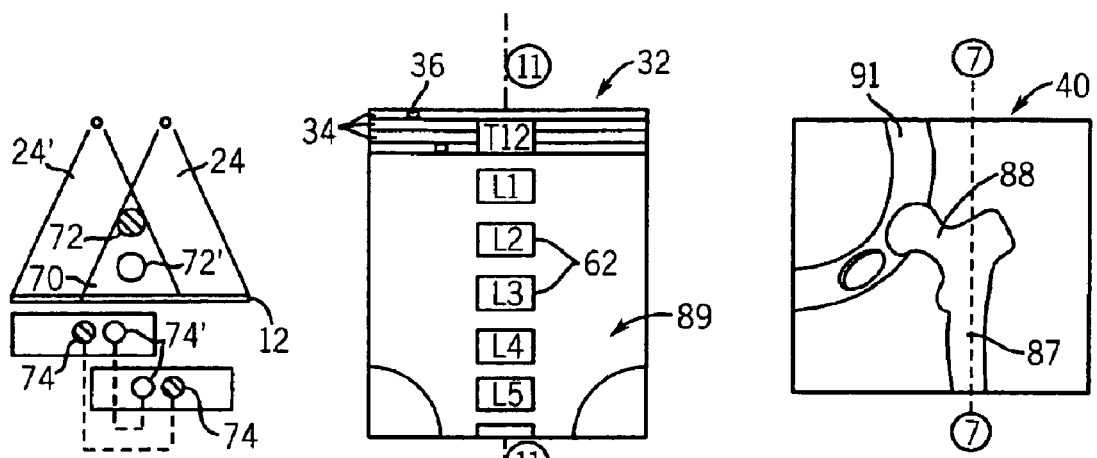
FIG. 2 is a geometric representation of two successive fan beams in the scanning pattern of FIG. 1 showing how height of a bone may be determined using shifts in the images produced by the divergent rays of the fan beams.
FIG. 3 is a bone image of the lumbar spine such as may be acquired from the apparatus of FIG. 1 showing its composition from scan lines obtained in the scans of FIGS. 1 and 2.
FIG. 4 is a figure similar to that of FIG. 3 showing a bone image for the proximal femur.

At each data point, the two measurements may be combined to produce separate bone and soft tissue images. Referring now to FIG. 3, a bone image 32 associated with a scan of the lower lumbar vertebrae may be composed of data of a variety of scan lines 34 associated with each of the rays detected by the x-ray detector 22. Bone density of other skeletal sites (for example the femur or the forearm) also may be measured. The measurements of each scan line produce a row of pixels 36 representing an areal bone density along the ray line of that measurement. The bone density may be mapped to a gray scale to present the bone image 32 on the terminal 28 to the operator.

In a typical study, images of one or both of two areas are obtained, of a scan area 37 of the lower lumbar spine 89 producing bone image 32, or of scan area 38 of either proximal femur 87 producing bone image 40 shown in FIG. 4.

Figure 14:
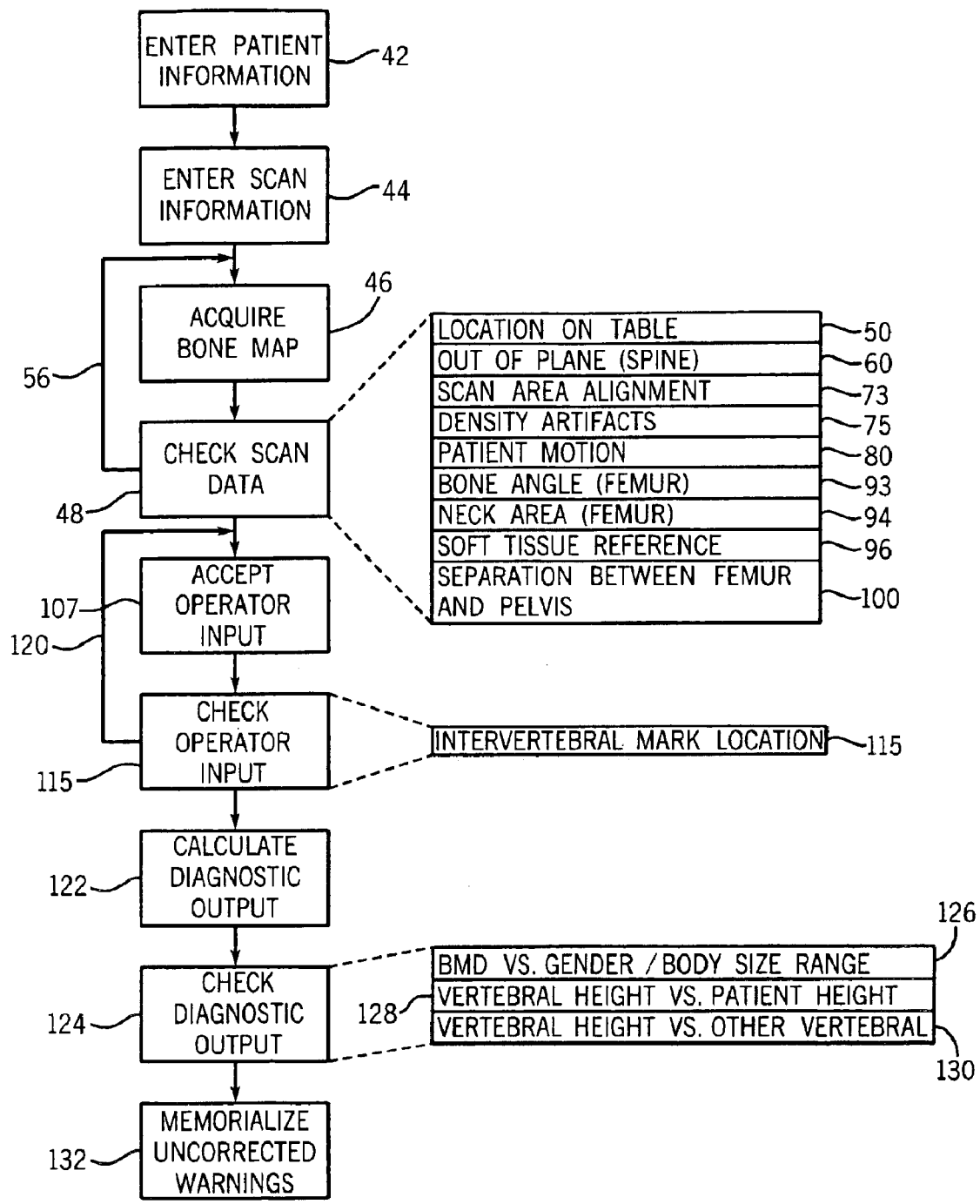
FIG. 14 is a flowchart showing various stages of the computer assistance envisioned by the present invention.

Referring now to FIGS. 1 and 14, the present invention provides a program executable by the computer 26 that assists the operator in ensuring high quality and accurate scans are obtained. At process block 42 and 44 the operator inputs, through a terminal 28, patient information including patient age, height, weight and gender as well as the particular scan area (37 or 38) being acquired.

The patient 14 is then positioned on the patient table 12 and the C-arm 18 moved to the scan area 37 or 38 as may be appropriate for the particular scan. The operator initiates the scan through the terminal 28 as indicated by process block 46.

The data acquired in the scan provides the first source of error, and therefore at process block 48, the scan data is checked. This checking process can be concurrent with the scan or performed at the conclusion of the scan. Generally, if the checking is performed during the scan, the particular steps of the check will be conducted repeatedly on all the data of bone images 32 or 40 acquired up to that instant. Otherwise, if the checking is performed after the scan, it is conducted on the entire bone image 32 or 40. Typically, when the checking is performed during the scan, it is also performed at the conclusion of the scan when a more comprehensive analysis can be performed.

The invention contemplates a number of checks of the scan data, not all of which need be performed in the invention. A first step 50 of this checking evaluates the location of the patient 14 on the table 12. Ideally, for the scan of the lower lumbar spine 89, the patient 14 is positioned so that the patient's spine 89 is centered on the table 12 and aligned with the longitudinal axis 16.

Figure 8:
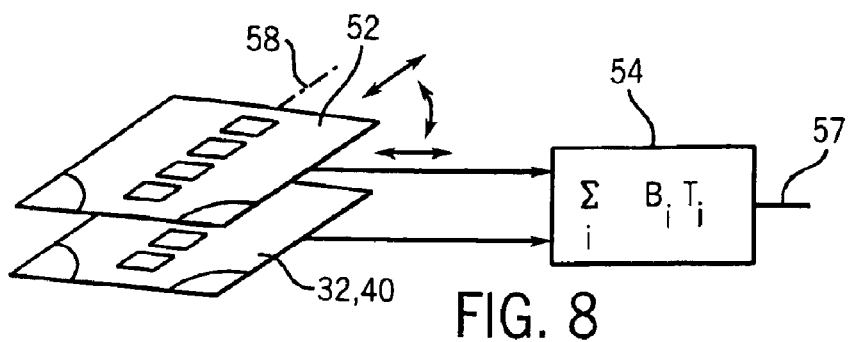
FIG. 8 is a schematic representation of the process of correlating a template with a bone image such as that of FIG. 3 to identify proper patient positioning and proper location of the scan area as well as positioning of various regions of interest used in other measurements of the image.

This checking of the spine 89, location can be performed in a variety of ways. In one embodiment, shown in FIG. 8, the bone image 32 or 40 is correlated with a template 52 providing a corresponding bone density image standardized to an average patient. The template 52 is mathematically shifted along the bone image 32 or 40 and the two images are correlated by a mathematical correlation process 54 that compares each pixel of the bone image 32 or 40 ($B_i$) with the aligned pixel of the template ($T_i$) over the entire image (i pixels). This process is performed by a correlator 54 realized in software on the computer 26 and is continued until the best alignment is obtained. The alignment process may include optionally not only translation laterally and in an inferior/superior direction, but also rotation and scaling to fit the template as accurately as possible to the scan data.

When maximum correlation is obtained, indicated by output 57 of the correlator 54, the location of the patient 14 can be obtained by reviewing the template's predetermined centerline 58 to determine the location of the patient's spine 89 or femur 87 with respect to the table 12 and relative angulation of each. Per step 50, if the angulation of the spine 89 or translation of the spine 89 or femur 87 on the table 12, as scanned, deviates by more than a predetermined about from the centerline of the table 12, a warning will be generated. Each such warning is provided to the operator to allow repeat of the acquisition as indicated by process branch 56.

The location of the template may also be used to define certain regions of analysis in the underlying bone image 32 and 40, and to determine angulation of the bones as may be used in later analysis steps to be described.

A second step 60 of checking the scan data as shown in FIG. 14, evaluates whether the bone is out of plane, that is, not parallel with the top of the patient table 12 (in the case of the spine 89) or the amount of angulation of the bone (in the case of the neck of the femur 87).

Figure 9:
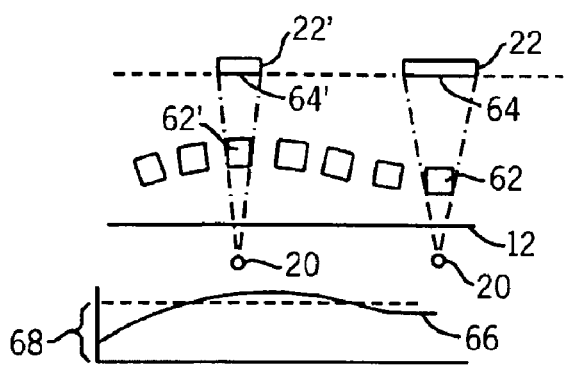
FIG. 9 is a simplified lateral view of a spine showing curvature away from the surface of the table such as creates magnification artifacts that may affect density measurements. This lateral view is positioned over a graph of vertebral height as deduced from the fan beam parallax per FIG. 2 such as may be used to trigger an operator warning condition.

Referring to FIG. 9, the spine 89 may arc upward away from the top of the patient table 12. Vertebrae 62 that are closer to the top of the patient table 12 and thus the x-ray source 20, will have greater magnification in the image 64 received by the x-ray detector 22 than vertebra 62", whose image 64" at the x-ray detector 22" will be smaller. The smaller image produces an apparent greater areal density, which may affect the integrity of the scan. Accordingly, the present invention may provide a measurement of spine height 66 as a function of longitudinal distance along the spine 89 that may be compared against a desired limit 68 and an operator warning if the spine height 66 exceeds this limit 68.

Referring now also to FIG. 2, the spine height 66 (or the height of any bone) may be deduced in a variety of manners including through a lateral scan of the patient. In the preferred embodiment of the present invention, however, the spine height 66 is deduced by analyzing a region of overlap 70 between two successive images obtained by fan beams 24 and 24" in successive transverse scans 33. Vertebra or other bones 72 that are further off the patient table 12 will produce more widely separated images 74 than bone 72' closer to the table surface, which produce less widely separated images 74'. Shifting the images 74 and 74' to obtain alignment in the overlap region of either bone 72 or bone 72' thus provides a triangulation giving a measurement of height of the bones 72, 72'.

Height determinations of this kind need only be made occasionally during the acquisition of the images 32 and 40 because of the slowly varying geometry of the bones and thus the overlap of the fan beams 24 and 24" need not equal the width of the entire fan beam 24.

Referring again to FIG. 14, the check of scan data per process block 48 may include the step 73 of evaluating whether the scan area 37 or 38 corresponds with the area of the patient 14 actually scanned. Referring again to FIG. 8, this may be done by checking the absolute magnitude of the greatest correlation between the selected template 52 and the particular bone image 32 or 40. Failure of a threshold correlation to be achieved may indicate that the patient region that was scanned is inappropriate.

Figure 5:
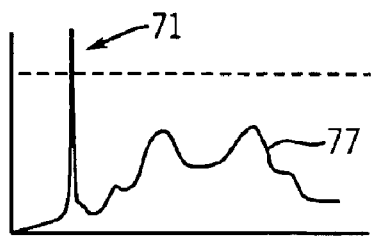
FIG. 5 is a plot of attenuation taken along one scan line of FIG. 3 showing an attenuation peak caused by a metallic foreign object in the proximity of the patient that creates a density artifact.

Step 75 searches for high-density artifacts caused, for example, by pins or metallic items in the patient 14 or on the patient's clothing or on surface of the table 12, such as buttons or clips. Referring to FIG. 5, these artifacts may be identified by extremely high attenuations 71 in a given scan line 77 of a bone image 32 or globally with respect to all data of a completed bone image 32. Additional or alternative filters may be applied to these data that evaluate not only the magnitude of the histogram but also its steepness and/or dual energy characteristics, as will be understood to those of ordinary skill in the art.

Figure 6:
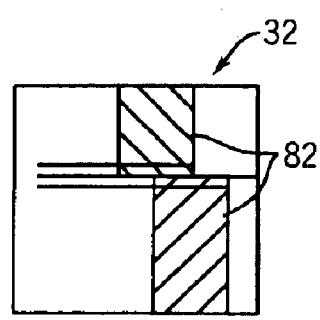
FIG. 6 is a detailed fragmentary view of the bone image of the femur per FIG. 4 showing a discontinuity caused by patient motion in a lateral direction during the scanning process.

Referring again to FIG. 14, an important source of errors in the acquired data, as checked at process block 48, may be patient motion, which may be evaluated as indicated by step 80. Referring to FIG. 6, lateral motion of the patient will be manifest in a bone image 32 or 40 as a discontinuity 82 in the vertical edges of the imaged bone. Bone edges are readily visible in the bone images 32 and 40 and may be further identified by prelocated analysis zones imprinted on the template 52 aligned with the underlying bone image 32. A mathematical derivative taken along the edges of the bone near the discontinuity 82 will identify the discontinuity 82 as a value exceeding a predetermined threshold, triggering a warning to the operator as well as a visual marking of the bone image 32 or 40. Again, this process may be performed upon completion of the scan or on a line-by-line basis.

Figure 7:
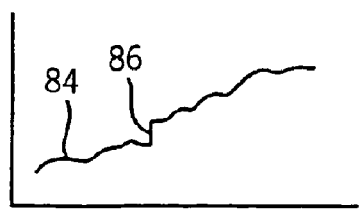
FIG. 7 is a plot similar to FIG. 5 of a column of data from the bone image of the femur taken along line 7—7 of FIG. 4 showing a discontinuity in density such as may indicate patient motion in a superior-inferior direction.

Superior-inferior patient motion, resulting in shifting a vertically oriented bone along a vertical axis, will not reveal pronounced discontinuities per FIG. 6 but will affect the density taken along the bone as shown in FIG. 7. Here, a general trend in the density as a function of distance 84 along the bone shows a discontinuity 86 at the moment of patient motion. Again, a simple differentiation process followed by a thresholding will indicate possible patient motion.

Referring again to FIGS. 14 and 4, a consideration in obtaining good scans of the femur 87 is that the neck 88 of the femur 87 be substantially horizontal so as to render an accurate bone density measurement without overlap with the pelvis or density artifacts caused by foreshortening. Angulation of the neck 88 may be determined through the height measurement technique described with respect to FIG. 2 or may be deduced by an anisotropic scaling of a template 52 during correlation that shortens its width disproportionately to its height. This checking of bone angle is indicated at step 93.

Figure 10:
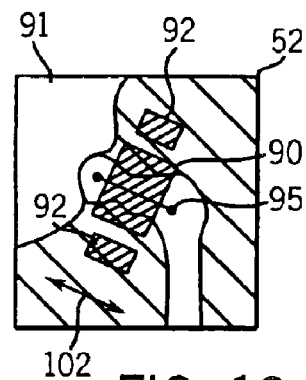
FIG. 10 is a simplified representation of a template per FIG. 8 having predefined regions of interest at the proximal femur that may be used to analyze the quality of the acquired data.

Referring now to FIG. 10, a template 52 for the proximal femur 87 is shown such as may be scaled, as described above, to the collected bone images 32 and 40 and which has embedded analysis zone 90 and two soft tissue measurement zones 92 used to guide analysis of the bone images 32 or 40 after the template 52 is properly aligned. Using the analysis zone 90, the neck 88 of the femur 87 may be analyzed per step 94 in FIG. 14 to see if sufficient neck area is available for accurate bone density measurement. If not, an operator warning is provided. In this case, area may be determined by a simple counting of bone in the analysis zone 90.

Similarly, as indicated by step 96, the availability of soft tissue zones 92 free from bone may be evaluated using the soft tissue measurement zones 92. Suitable soft tissue is determined by counting soft tissue pixels in the soft tissue measurement zones 92. A certain amount of soft tissue is necessary to provide an accurate reference to calibrate the bone density measurements, as is understood in the art.

Referring now to FIG. 14 and FIG. 10, a final step in the analysis of the scan data 100 investigates whether there is sufficient separation (distance 102) between the femur 87 and the pelvis 91. This analysis, again, may use the correlated and scaled template 52, to review the length of an embedded separation line 95 in the template 52 after scaling.

Referring again to FIG. 4, these measurements may alternatively be performed by fiducial points marked by the operator on the bone images 32, as prompted by the computer 26, or by other image recognition techniques such as, for example, those which identify fiducial points such as the lesser or greater trochanter neck and other landmark features in the particular scanned regions.

Returning to FIG. 14, once the data have been acquired at process block 46 and confirmed at process block 48, the program may proceed to process block 107 where operator input is accepted for analysis purposes. If at process block 48 the scan data is not approved, that is it fails one or more of the steps 50, 60, 73, 75, 80, 93, 94, 96, and 100), the operator may nevertheless proceed to provide analysis of the data at process block 107. The data, however, will be marked to indicate possible artifacts.

Figure 11:
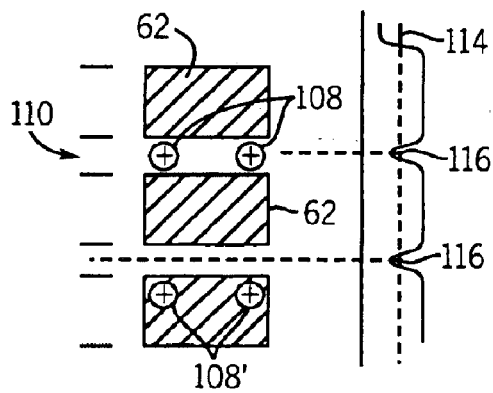
FIG. 11 is a graphical representation of the bone image of lumbar vertebrae such as may be displayed to the operator to allow positioning of intervertebral fiducial points for the segmentation of the vertebral bodies to determine bone density The graphical representation is positioned next to a plot of bone density along the centerline of the vertebrae whose minimums can be used to analyze operator located intervertebral points.
Figure 12:
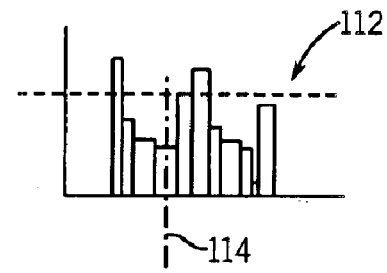
FIG. 12 is a histogram of density values used to determine the threshold for defining intervertebral spaces in FIG. 11.

At process block 107, the operator may provide input to allow the analysis of the data. Referring to FIGS. 14 and 11, at step 115 of FIG. 14, this operator input data may, for example, be the placement of markers 108 in the intervertebral spaces 110 between vertebrae 62. The placement of these markers 108 may be done by manipulation of the cursor control device 35 according to techniques known in the art.

Figure 13:
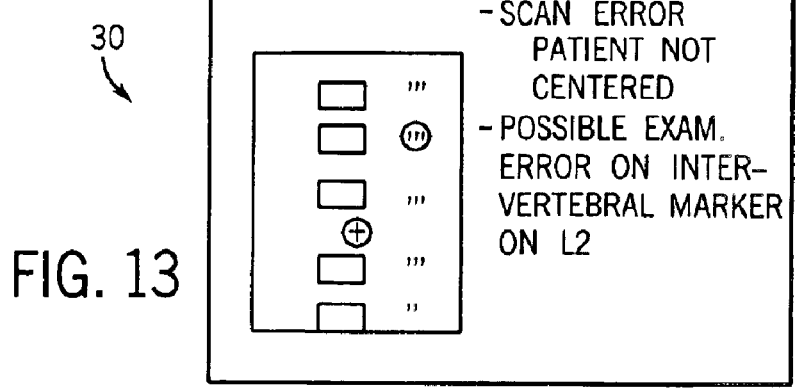
FIG. 13 is a sample operator screen showing indications to the operator of possible errors.

Such intervertebral markers 106 determine the measurement of vertebral height, which is necessary to compute vertebral area and determine if a particular vertebra 62 has had a crush fracture. The location by the operator of the intervertebral markers 108 may be checked by software review of the underlying data of the bone image 32. Referring momentarily to FIG. 9, the bone density data of the bone image 32, collected up to the time of the check, may be plotted in a histogram 112, which may be used to make a determination of a boundary 114 between bone and soft tissue. This boundary 114 may be applied to row-averaged bone density data of the bone image 32 in the area of the spine (aligned generally along line 11—11 through FIG. 3) to determine points of minima 116 corresponding with the intervertebral spaces 110. Referring also to FIG. 13, to the extent that the operator places intervertebral markers 108" in locations that deviate significantly from the minima 116, the operator will be notified in the checking process 118 shown in FIG. 14 so as to have the opportunity to re-input the data as indicated by the process path 120. Notification may be by text messages and/or highlighting of the misplaced markers or erroneous operator data.

The operator may then proceed to calculation of diagnostic output at process block 122, in this case measurements of bone area, bone content, bone density, and vertebral height, either after a correction of the operator input or a notation that the input was not corrected (if a correction was suggested by the program).

At succeeding block 124, the diagnostic output (in this case vertebral height) is checked against standard output ranges as a final safety check on the data. Typically, the diagnostic output of a densitometer will be either a bone mineral density reading in grams per square centimeter or a T-score or Z-score, the former being the number of standard deviations of the diagnostic output from a reading expected of a healthy 30-year old standard woman and the latter being the number of standard deviations of the diagnostic output from an age-adjusted standard woman.

Specifically, as indicated by step 126, the computer 26 may store an expected range of clinically experienced BMDs, T-scores, or Z-scores and compare the diagnostic output against these to flag a problem if the diagnostic output is outside of this range.

As indicated by step 128, a similar process may be used to check diagnostic outputs of vertebral height used in assessing possible crush fractures or other morphometric aspects of the vertebra. Here, the diagnostic output may be compared against patient height or against other vertebra of the patient above and below the given vertebra or against an average of the patient's vertebrae used to define a range within which the diagnostic output reading should fall. Generally, a crush fracture will cause a deviation of vertebra height from its neighbors, but the ranges are established to embrace the normal expected deviation.

At step, 132 the report is generated which may include images marked as described above and warnings that were not corrected per branch 56 and 120.

It is specifically intended that the present invention not be limited to the embodiments and illustrations contained herein, but include modified forms of those embodiments including portions of the embodiments and combinations of elements of different embodiments as come within the scope of the following claims.

What is claimed is:

1. A computer aided bone densitometry system comprising:
    an x-ray source and detector opposable about a patient to produce signals indicating x-ray attenuation by bone of the patient;
    a computer receiving the signals and executing a stored program to:
    (a) control the x-ray source and detector to signals for a plurality of points over a scan area;
    (b) calculate, for the plurality of points, a bone mineral data set indicating x-ray attenuation caused by bone;
    (c) measure the bone mineral data set to evaluate the likelihood that acquisition of the signals was faulty; and
    (d) output an indication of faulty data acquisition to the operator when the evaluation of the bone mineral data set indicates that the acquired data is likely faulty.

2. The computer aided densitometer of claim 1 wherein the measurement of the bone mineral data set compares peak attenuations in the bone mineral data set with an expected peak attenuation to detect faulty acquisition caused by foreign objects with high density.

3. The computer aided densitometer of claim 1 wherein the measurement of the bone mineral data set detects patient motion causing faulty acquisition.

4. The computer aided densitometer of claim 3 wherein the measurement of the bone mineral data set calculates discontinuities in bone edges to detect patient motion.

5. The computer aided densitometer of claim 3 wherein the measurement of the bone mineral data set calculates jumps in density within a bone to detect patient motion.

6. The computer aided densitometer of claim 1 wherein the measurement of the bone mineral data set detects mispositioning of the scan area on the patient causing faulty acquisition.

7. The computer aided densitometer of claim 6 wherein the measurement of the bone mineral data set calculates a difference between the location of bones represented by the bone mineral data set and an expected location of the bones to detect mispositioning of the scan area on the patient.

8. The computer aided densitometer of claim 6 wherein the measurement of the bone mineral data set detects mispositioning of the scan area with respect to the vertebrae of the spine.

9. The computer aided densitometer of claim 6 wherein the measurement of the bone mineral data set detects mispositioning of the scan area with respect to the proximal femur.

10. The computer aided densitometer of claim 1 wherein the patient is supported horizontally on a table and wherein the scan area encompasses the spine wherein the measurement of the bone mineral data set detects excessive displacement of the spine from a center of the table causing faulty acquisition.

11. The computer aided densitometer of claim 1 wherein the patient is supported horizontally on a table and wherein the scan area encompasses the spine wherein the measurement of the bone mineral data set detects angulation of the spine from parallel with a long axis of the table causing faulty acquisition.

12. The computer aided densitometer of claim 1 wherein the patient is supported horizontally on a table and wherein the scan area encompasses the spine wherein the measurement of the bone mineral data set detects mispositioning of the spine with respect to a supporting surface of the table causing faulty acquisition.

13. The computer aided densitometer of claim 1 wherein the scan area covers the proximal femur and wherein the measurement of the bone mineral data set detects separation between the femur and the pelvis to detect mispositioning of the patient trunk with respect to the patient's leg causing faulty acquisition.

14. The computer aided densitometer of claim 1 wherein the scan area covers the proximal femur and wherein the measurement of the bone mineral data set detects lack of soft tissue reference areas causing faulty acquisition.

15. The computer aided densitometer of claim 1 wherein the scan area covers the proximal femur and wherein the measurement of the bone mineral data set detects the measured area of the neck region of the femur.

16. A computer aided bone densitometry system comprising:
    an x-ray source and detector opposable about a patient to provide signals indicating x-ray attenuation by bone of the patient;
    a computer receiving the signals and executing a stored program to:
    (a) control the x-ray source and detector to acquire signals for a plurality of points over a scan area;
    (b) calculate, for the plurality of points, a bone mineral data set indicating x-ray attenuation caused by bone;
    (c) accept operator input to define portions of the bone mineral data set for quantitative measurement;
    (d) compare the portions of the bone mineral data defined by operator input to portions automatically derived from the bone mineral data set; and
    (e) output an indication to the operator if the operator input deviates from the automatically derived input by more than a predetermined amount.

17. The computer aided densitometer of claim 15 wherein the operator input defines intervertebral locations for vertebral height and bone mineral density measurement.

18. A computer aided densitometry system comprising:

an x-ray source and detector opposable about a patient to provide signals indicating x-ray attenuation by tissue of the patient;

a computer receiving the signals and executing a stored program to;

(a) control the x-ray source and detector to acquire signals through a patient for a plurality of points over a scan area;

(b) calculate, for the plurality of points, a bone mineral data set indicating x-ray attenuation caused by bone;

(c) analyze the bone mineral data set to produce a value indication of bone health;

(d) compare the value indication of bone health to a standard range of values; and (e) output an indication to the operator that the indication of bone health may be erroneous if the value indication is outside the standard range.

19. The computer aided densitometer of claim 18 wherein the indication of bone health is bone density and wherein the program further accepts from an operator patient information selected from the group consisting of patient gender, patient age, patient height, and patient weight and wherein the standard range is adjusted according to the patient information.

20. The computer aided densitometer of claim 18 wherein the indication of bone health is vertebral height and wherein the program further accepts from an operator patient height and wherein the standard range is adjusted according to the patient height.

21. The computer aided densitometer of claim 18 wherein the indication of bone health is vertebral height and wherein the standard range is adjusted according to the measurement of adjacent vertebra of the patient.

22. The computer aided densitometer of claim 18 wherein the indication of bone health is vertebral height and wherein the standard range is adjusted according to the measurement of average of other vertebra of the patient.

* * * * *